US009510739B2

(12) United States Patent
Adler

(10) Patent No.: US 9,510,739 B2
(45) Date of Patent: Dec. 6, 2016

(54) ENDOSCOPE SMALL IMAGING SYSTEM

(71) Applicant: GYRUS ACMI INC., Southborough, MA (US)

(72) Inventor: Doron Adler, Haifa (IL)

(73) Assignee: GYRUS ACMI, INC., Southborough, MA (US)

( * ) Notice: Subject to any disclaimer, the term of this patent is extended or adjusted under 35 U.S.C. 154(b) by 237 days.

(21) Appl. No.: 13/940,282

(22) Filed: Jul. 12, 2013

(65) Prior Publication Data

US 2015/0015687 A1    Jan. 15, 2015

(51) Int. Cl.
*A61B 1/04* (2006.01)
*A61B 1/05* (2006.01)
*A61B 1/00* (2006.01)
*H04N 5/225* (2006.01)

(52) U.S. Cl.
CPC ............ *A61B 1/04* (2013.01); *A61B 1/00096* (2013.01); *A61B 1/00163* (2013.01); *A61B 1/05* (2013.01); *H04N 2005/2255* (2013.01); *Y10T 29/49826* (2015.01)

(58) Field of Classification Search
CPC  A61B 1/04; A61B 1/00096; A61B 1/00163; A61B 1/05; Y10T 29/49826; H04N 2005/2255
See application file for complete search history.

(56) References Cited

U.S. PATENT DOCUMENTS

| 3,321,656 | A | 5/1967 | Sheldon |
| 3,971,065 | A | 7/1976 | Bayer |
| 4,253,447 | A | 3/1981 | Moore et al. |
| 4,261,344 | A | 4/1981 | Moore et al. |
| 4,278,077 | A | 7/1981 | Mizumoto |
| 4,429,328 | A | 1/1984 | Jones, Jr. et al. |
| 4,467,361 | A | 8/1984 | Ohno et al. |
| 4,491,865 | A | 1/1985 | Danna et al. |

(Continued)

FOREIGN PATENT DOCUMENTS

| DE | 4243452 A1 | 6/1994 |
| DE | 19851993 A1 | 6/1999 |

(Continued)

OTHER PUBLICATIONS

International Application # PCT/US14/42825 Search Report dated Oct. 6, 2014.

(Continued)

*Primary Examiner* — Thai Tran
*Assistant Examiner* — Christopher T Braniff
(74) *Attorney, Agent, or Firm* — D. Kligler I.P. Services Ltd.

(57) ABSTRACT

An endoscope camera, including a cylindrical enclosure having an enclosure diameter, and an imaging array mounted within the enclosure so that a plane face of the imaging array is parallel to the enclosure diameter. The camera includes a right-angle transparent prism having a rectangular entrance face, an exit face, and an hypotenuse configured to reflect radiation from the entrance face to the exit face. The entrance face has a first edge longer than a second edge, and the prism is mounted within the enclosure so that the first edge is parallel to the enclosure diameter and so that the exit face mates with the plane face of the imaging array. The camera further includes optics, configured to receive incoming radiation from an object, which are mounted so as to transmit the incoming radiation to the imaging array via the entrance and exit faces of the prism.

20 Claims, 8 Drawing Sheets

(56) References Cited

U.S. PATENT DOCUMENTS

| | | | |
|---|---|---|---|
| 4,555,768 | A | 11/1985 | Lewis, Jr. et al. |
| 4,569,335 | A | 2/1986 | Tsuno |
| 4,573,450 | A | 3/1986 | Arakawa |
| 4,576,146 | A | 3/1986 | Kawazoe et al. |
| 4,602,281 | A | 7/1986 | Nagasaki et al. |
| 4,604,992 | A | 8/1986 | Sato |
| 4,622,954 | A | 11/1986 | Arakawa et al. |
| 4,625,236 | A | 11/1986 | Fujimori et al. |
| 4,633,304 | A | 12/1986 | Nagasaki |
| 4,643,170 | A | 2/1987 | Miyazaki et al. |
| 4,646,721 | A | 3/1987 | Arakawa |
| 4,651,201 | A | 3/1987 | Schoolman |
| 4,656,508 | A | 4/1987 | Yokota |
| 4,682,219 | A | 7/1987 | Arakawa |
| 4,684,222 | A | 8/1987 | Borrelli et al. |
| 4,692,608 | A | 9/1987 | Cooper et al. |
| 4,697,208 | A | 9/1987 | Eino |
| 4,710,807 | A | 12/1987 | Chikama |
| 4,713,683 | A | 12/1987 | Fujimori et al. |
| 4,714,319 | A | 12/1987 | Zeevi et al. |
| 4,720,178 | A | 1/1988 | Nishioka et al. |
| 4,741,327 | A | 5/1988 | Yabe |
| 4,745,470 | A | 5/1988 | Yabe et al. |
| 4,746,203 | A | 5/1988 | Nishioka et al. |
| 4,757,805 | A | 7/1988 | Yabe |
| 4,768,513 | A | 9/1988 | Suzuki |
| 4,784,133 | A | 11/1988 | Mackin |
| 4,803,550 | A | 2/1989 | Yabe et al. |
| 4,803,562 | A | 2/1989 | Eino |
| 4,809,680 | A | 3/1989 | Yabe |
| 4,819,065 | A | 4/1989 | Eino |
| 4,827,907 | A | 5/1989 | Tashiro |
| 4,827,909 | A | 5/1989 | Kato et al. |
| 4,831,456 | A | 5/1989 | Takamura et al. |
| 4,832,003 | A | 5/1989 | Yabe |
| 4,832,033 | A | 5/1989 | Maher et al. |
| 4,857,724 | A | 8/1989 | Snoeren |
| 4,862,873 | A | 9/1989 | Yajima et al. |
| 4,866,526 | A | 9/1989 | Ams et al. |
| 4,869,256 | A | 9/1989 | Kanno et al. |
| 4,873,572 | A | 10/1989 | Miyazaki et al. |
| 4,884,133 | A | 11/1989 | Kanno et al. |
| 4,890,159 | A * | 12/1989 | Ogiu .............. A61B 1/00045 348/231.99 |
| 4,905,670 | A | 3/1990 | Adair |
| 4,926,257 | A | 5/1990 | Miyazaki |
| 4,934,339 | A | 6/1990 | Kato |
| 4,939,573 | A | 7/1990 | Teranishi et al. |
| 4,953,539 | A | 9/1990 | Nakamura et al. |
| 4,967,269 | A | 10/1990 | Sasagawa et al. |
| 4,986,642 | A | 1/1991 | Yokota et al. |
| 4,998,972 | A | 3/1991 | Chin et al. |
| 5,010,875 | A | 4/1991 | Kato |
| 5,021,888 | A | 6/1991 | Kondou et al. |
| 5,022,399 | A | 6/1991 | Biegelisen |
| 5,029,574 | A | 7/1991 | Shimamura et al. |
| 5,122,650 | A | 6/1992 | McKinley |
| 5,144,442 | A | 9/1992 | Ginosar et al. |
| 5,166,787 | A | 11/1992 | Irion |
| 5,184,223 | A | 2/1993 | Mihara |
| 5,187,572 | A | 2/1993 | Nakamura et al. |
| 5,191,203 | A | 3/1993 | McKinley |
| 5,216,512 | A * | 6/1993 | Bruijns .............. H04N 3/155 250/216 |
| 5,219,292 | A | 6/1993 | Dickirson et al. |
| 5,222,477 | A | 6/1993 | Lia |
| 5,233,416 | A | 8/1993 | Inoue |
| 5,264,925 | A | 11/1993 | Shipp et al. |
| 5,294,986 | A | 3/1994 | Tsuji et al. |
| 5,301,090 | A | 4/1994 | Hed |
| 5,306,541 | A | 4/1994 | Kasatani |
| 5,311,600 | A | 5/1994 | Aghajan et al. |
| 5,323,233 | A | 6/1994 | Yamagami et al. |
| 5,325,847 | A | 7/1994 | Matsuno |
| 5,335,662 | A | 8/1994 | Kimura et al. |
| 5,343,254 | A | 8/1994 | Wada et al. |
| 5,363,135 | A | 11/1994 | Inglese |
| 5,365,268 | A | 11/1994 | Minami |
| 5,376,960 | A | 12/1994 | Wurster |
| 5,381,784 | A | 1/1995 | Adair |
| 5,408,268 | A | 4/1995 | Shipp |
| 5,430,475 | A | 7/1995 | Goto et al. |
| 5,432,543 | A | 7/1995 | Hasegawa et al. |
| 5,436,655 | A | 7/1995 | Hiyama et al. |
| 5,444,574 | A | 8/1995 | Ono et al. |
| 5,450,243 | A | 9/1995 | Nishioka |
| 5,471,237 | A | 11/1995 | Shipp |
| 5,494,483 | A | 2/1996 | Adair |
| 5,498,230 | A | 3/1996 | Adair |
| 5,512,940 | A | 4/1996 | Takasugi et al. |
| 5,547,455 | A | 8/1996 | McKenna et al. |
| 5,557,324 | A | 9/1996 | Wolff |
| 5,575,754 | A | 11/1996 | Konomura |
| 5,577,991 | A | 11/1996 | Akui et al. |
| 5,588,948 | A * | 12/1996 | Takahashi .......... A61B 1/00179 348/45 |
| 5,594,497 | A | 1/1997 | Ahern et al. |
| 5,598,205 | A * | 1/1997 | Nishioka .................. A61B 1/05 348/335 |
| 5,603,687 | A | 2/1997 | Hori et al. |
| 5,604,531 | A | 2/1997 | Iddan et al. |
| 5,607,436 | A | 3/1997 | Pratt et al. |
| 5,668,596 | A | 9/1997 | Vogel |
| 5,673,147 | A | 9/1997 | McKinley |
| 5,700,236 | A | 12/1997 | Sauer et al. |
| 5,712,493 | A | 1/1998 | Mori et al. |
| 5,728,044 | A | 3/1998 | Shan |
| 5,734,418 | A | 3/1998 | Danna |
| 5,751,341 | A | 5/1998 | Chaleki et al. |
| 5,754,280 | A | 5/1998 | Kato et al. |
| 5,784,098 | A | 7/1998 | Shoji et al. |
| 5,792,045 | A | 8/1998 | Adair |
| 5,797,837 | A | 8/1998 | Minami |
| 5,819,736 | A | 10/1998 | Avny et al. |
| 5,827,176 | A | 10/1998 | Tanaka et al. |
| 5,847,394 | A | 12/1998 | Alfano et al. |
| 5,905,597 | A | 5/1999 | Mizouchi et al. |
| 5,907,178 | A | 5/1999 | Baker et al. |
| 5,909,633 | A | 6/1999 | Haji et al. |
| 5,928,137 | A | 7/1999 | Green |
| 5,929,901 | A | 7/1999 | Adair et al. |
| 5,940,126 | A | 8/1999 | Kimura |
| 5,944,655 | A | 8/1999 | Becker |
| 5,984,860 | A | 11/1999 | Shan |
| 5,986,693 | A | 11/1999 | Adair et al. |
| 6,001,084 | A | 12/1999 | Riek et al. |
| 6,006,119 | A | 12/1999 | Soller et al. |
| 6,009,189 | A | 12/1999 | Schaack |
| 6,010,449 | A | 1/2000 | Selmon et al. |
| 6,039,693 | A | 3/2000 | Seward et al. |
| 6,043,839 | A | 3/2000 | Adair et al. |
| 6,075,235 | A | 6/2000 | Chun |
| 6,099,475 | A | 8/2000 | Seward et al. |
| 6,100,920 | A | 8/2000 | Miller et al. |
| 6,124,883 | A | 9/2000 | Suzuki et al. |
| 6,128,525 | A | 10/2000 | Zeng et al. |
| 6,129,672 | A | 10/2000 | Seward et al. |
| 6,130,724 | A | 10/2000 | Hwang |
| 6,134,003 | A | 10/2000 | Tearney et al. |
| 6,139,490 | A | 10/2000 | Breidenthal et al. |
| 6,142,930 | A | 11/2000 | Ito et al. |
| 6,148,227 | A | 11/2000 | Wagnieres et al. |
| 6,156,626 | A | 12/2000 | Bothra |
| 6,177,984 | B1 | 1/2001 | Jacques |
| 6,178,346 | B1 | 1/2001 | Amundson et al. |
| 6,184,923 | B1 | 2/2001 | Miyazaki |
| 6,206,825 | B1 | 3/2001 | Tsuyuki |
| 6,240,312 | B1 | 5/2001 | Alfano et al. |
| 6,260,994 | B1 | 7/2001 | Matsumoto et al. |
| 6,281,506 | B1 | 8/2001 | Fujita et al. |
| 6,284,223 | B1 | 9/2001 | Luiken |
| 6,327,374 | B1 | 12/2001 | Piironen et al. |
| 6,331,156 | B1 | 12/2001 | Haefele et al. |
| 6,409,658 | B1 | 6/2002 | Mitsumori |

(56) References Cited

U.S. PATENT DOCUMENTS

| | | |
|---|---|---|
| 6,416,463 B1 | 7/2002 | Tsuzuki et al. |
| 6,417,885 B1 | 7/2002 | Suzuki et al. |
| 6,449,006 B1 | 9/2002 | Shipp |
| 6,459,919 B1 | 10/2002 | Lys et al. |
| 6,464,633 B1 | 10/2002 | Hosoda et al. |
| 6,476,851 B1 | 11/2002 | Nakamura |
| 6,485,414 B1 | 11/2002 | Neuberger |
| 6,533,722 B2 | 3/2003 | Nakashima |
| 6,547,721 B1 | 4/2003 | Higuma et al. |
| 6,659,940 B2 | 12/2003 | Adler |
| 6,670,636 B2 | 12/2003 | Hayashi et al. |
| 6,692,430 B2 | 2/2004 | Adler |
| 6,697,110 B1 | 2/2004 | Jaspers et al. |
| 6,900,527 B1 | 5/2005 | Miks et al. |
| 6,943,837 B1 | 9/2005 | Booth |
| 6,976,956 B2 | 12/2005 | Takahashi et al. |
| 6,984,205 B2 | 1/2006 | Gazdzinski |
| 7,019,387 B1 | 3/2006 | Miks et al. |
| 7,030,904 B2 | 4/2006 | Adair et al. |
| 7,106,910 B2 | 9/2006 | Acharya et al. |
| 7,116,352 B2 | 10/2006 | Yaron |
| 7,123,301 B1 | 10/2006 | Nakamura et al. |
| 7,127,280 B2 | 10/2006 | Dauga |
| 7,133,073 B1 | 11/2006 | Neter |
| 7,154,527 B1 | 12/2006 | Goldstein et al. |
| 7,189,971 B2 | 3/2007 | Spartiotis et al. |
| 7,308,296 B2 | 12/2007 | Lys et al. |
| 7,347,817 B2 | 3/2008 | Glukhovsky et al. |
| 7,355,625 B1 | 4/2008 | Mochida et al. |
| 7,804,985 B2 | 9/2010 | Szawerenko et al. |
| 8,179,428 B2 | 5/2012 | Minami |
| 8,194,121 B2 | 6/2012 | Blumzvig et al. |
| 8,263,438 B2 | 9/2012 | Seah et al. |
| 8,438,730 B2 | 5/2013 | Ciminelli |
| 2001/0017649 A1 | 8/2001 | Yaron |
| 2001/0031912 A1 | 10/2001 | Adler |
| 2001/0040211 A1 | 11/2001 | Nagaoka |
| 2001/0051766 A1 | 12/2001 | Gazdzinski |
| 2002/0089586 A1 | 7/2002 | Suzuki et al. |
| 2002/0103417 A1 | 8/2002 | Gazdzinski |
| 2002/0154215 A1 | 10/2002 | Schechterman et al. |
| 2002/0198439 A1 | 12/2002 | Mizuno |
| 2003/0171648 A1 | 9/2003 | Yokoi et al. |
| 2003/0171649 A1 | 9/2003 | Yokoi et al. |
| 2003/0171652 A1 | 9/2003 | Yokoi et al. |
| 2003/0174208 A1 | 9/2003 | Glukhovsky et al. |
| 2003/0174409 A1 | 9/2003 | Nagaoka |
| 2004/0019255 A1 | 1/2004 | Sakiyama |
| 2004/0197959 A1 | 10/2004 | Ujiie et al. |
| 2005/0165279 A1 | 7/2005 | Adler et al. |
| 2005/0259487 A1 | 11/2005 | Glukhovsky et al. |
| 2005/0267328 A1 | 12/2005 | Blumzvig et al. |
| 2006/0158512 A1 | 7/2006 | Iddan et al. |
| 2008/0229573 A1 | 9/2008 | Wood et al. |
| 2009/0147076 A1 | 6/2009 | Ertas |
| 2009/0266598 A1 | 10/2009 | Katagiri et al. |
| 2009/0294978 A1 | 12/2009 | Ota et al. |
| 2010/0283818 A1 | 11/2010 | Bruce et al. |
| 2011/0210441 A1 | 9/2011 | Lee et al. |
| 2012/0161312 A1 | 6/2012 | Hossain et al. |
| 2012/0274705 A1 | 11/2012 | Petersen et al. |
| 2013/0129334 A9 | 5/2013 | Wang et al. |
| 2014/0249368 A1* | 9/2014 | Hu ................... H04N 5/2253 600/109 |

FOREIGN PATENT DOCUMENTS

| | | |
|---|---|---|
| EP | 1661506 A1 | 5/2006 |
| GB | 1215383 A | 12/1970 |
| JP | 5944775 A | 3/1984 |
| JP | 6215514 A | 1/1987 |
| JP | 0882751 A | 3/1996 |
| JP | H09-173288 A | 7/1997 |
| JP | 2006141884 A | 6/2006 |
| WO | 9417493 A1 | 8/1994 |
| WO | 9641481 A1 | 12/1996 |
| WO | 98/48449 A2 | 10/1998 |
| WO | 0033727 A1 | 6/2000 |
| WO | 2013/073578 A1 | 5/2013 |

OTHER PUBLICATIONS

International Application PCT/US2014/042826 Search Report dated Sep. 8, 2014.
Finkman et al., U.S. Appl. No. 13/933,145, filed Jul. 2, 2013.
U.S. Appl. No. 14/179,577 Office Action dated Oct. 13, 2015.
JP Application # 2015-563153 Office Action dated Jul. 15, 2016.

* cited by examiner

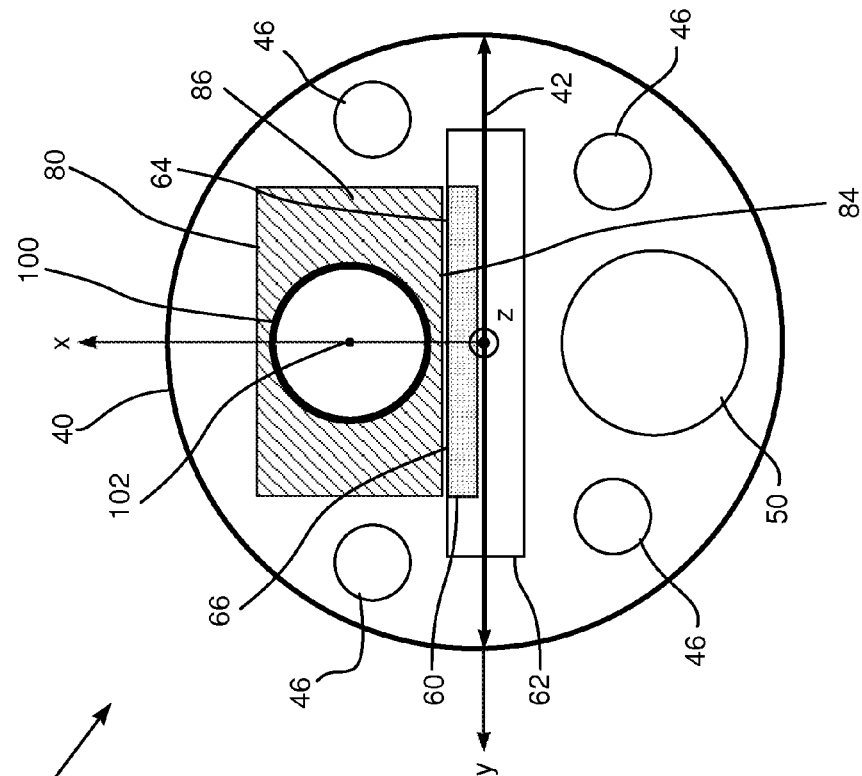
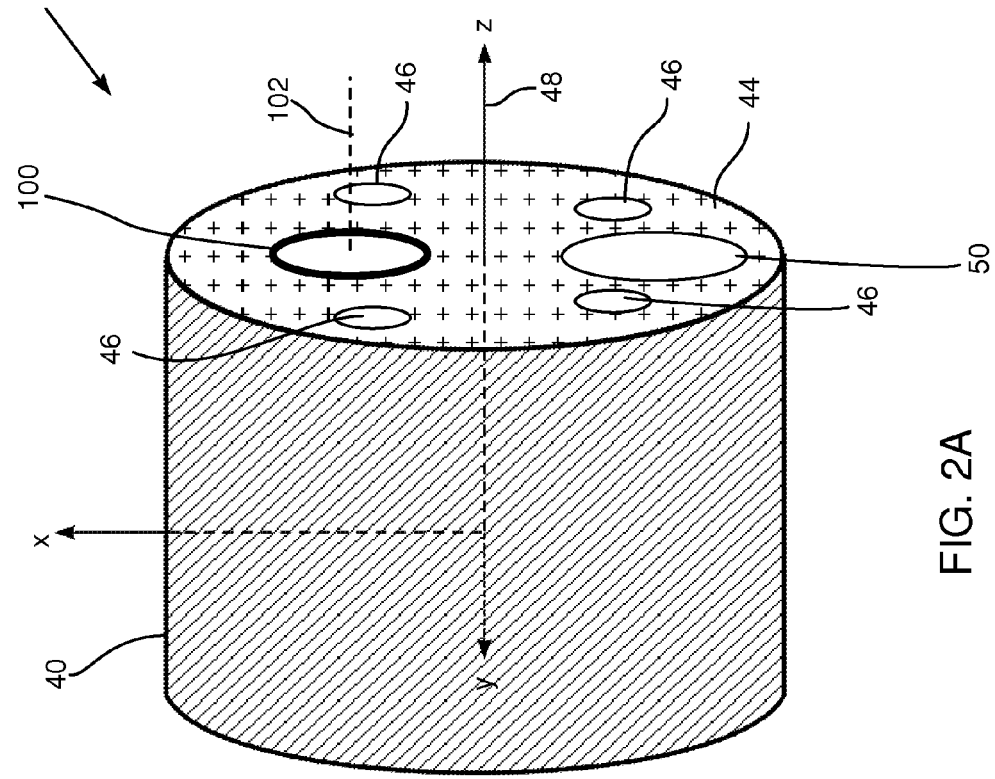

ENDOSCOPE SMALL IMAGING SYSTEM

FIELD OF THE INVENTION

The present invention relates generally to imaging, and specifically to imaging using an endoscope having a small external diameter.

BACKGROUND OF THE INVENTION

U.S. Pat. No. 8,179,428, to Minami et al., whose disclosure is incorporated herein by reference, describes an imaging apparatus for an electronic endoscope which uses a "bare chip" of a CCD (charge coupled device) together with a circuit board having approximately the same thickness as the bare chip.

U.S. Pat. No. 6,659,940, to Adler, whose disclosure is incorporated herein by reference, describes an endoscope having restricted dimensions. The endoscope has an image "gatherer," an image distorter, and an image sensor shaped to fit within the restricted dimensions.

U.S. Pat. No. 4,684,222, to Borelli et al., whose disclosure is incorporated herein by reference, describes a method for producing small lenses which may be formed to be anamorphic.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

SUMMARY OF THE INVENTION

An embodiment of the present invention provides an endoscope camera, including:

a cylindrical enclosure having an enclosure diameter;

an imaging array mounted within the enclosure so that a plane face of the imaging array is parallel to the enclosure diameter;

a right-angle transparent prism having a rectangular entrance face, an exit face, and an hypotenuse configured to reflect radiation from the entrance face to the exit face, the entrance face having a first edge longer than a second edge, the prism being mounted within the enclosure so that the first edge is parallel to the enclosure diameter and so that the exit face mates with the plane face of the imaging array; and optics, configured to receive incoming radiation from an object, mounted so as to transmit the incoming radiation to the imaging array via the entrance and exit faces of the prism.

In a disclosed embodiment the optics include gradient-index (GRIN) optics.

Typically, the optics have a circular cross-section.

In a further disclosed embodiment the imaging array is rectangular having sides equal to the first edge and the second edge.

Typically, the optics focus the incoming radiation to have a first magnification and a second magnification orthogonal to and different from the first magnification. An optics-ratio of the first magnification to the second magnification may be responsive to a prism-ratio of the first edge to the second edge. Alternatively or additionally, a ratio of the first magnification to the second magnification may be responsive to an aspect ratio of an object imaged by the camera.

In a yet further disclosed embodiment the optics introduce a distortion into an image, of an object, acquired by the imaging array so as to produce a distorted image thereon, and the camera includes a processor which applies an un-distortion factor to the distorted image so as to produce an undistorted image of the object. Typically, the distortion includes an optical distortion, and the processor is configured to apply the un-distortion factor as a numerical factor.

In an alternative embodiment the right-angle transparent prism includes an isosceles prism.

In a further alternative embodiment the imaging array is mounted so that an axis of the cylindrical enclosure is parallel to the plane face of the imaging array.

In a yet further alternative embodiment the imaging array is square having a side equal to the first edge.

There is further provided, according to an embodiment of the present invention, a method for forming an endoscope camera, including:

providing a cylindrical enclosure having an enclosure diameter;

mounting an imaging array within the enclosure so that a plane face of the imaging array is parallel to the enclosure diameter;

mounting a right-angle transparent prism within the enclosure, the prism having a rectangular entrance face, an exit face, and an hypotenuse configured to reflect radiation from the entrance face to the exit face, the entrance face having a first edge longer than a second edge, the prism being mounted within the enclosure so that the first edge is parallel to the enclosure diameter and so that the exit face mates with the plane face of the imaging array;

configuring optics to receive incoming radiation from an object; and mounting the optics so as to transmit the incoming radiation to the imaging array via the entrance and exit faces of the prism.

The present invention will be more fully understood from the following detailed description of the embodiments thereof, taken together with the drawings in which:

BRIEF DESCRIPTION OF THE DRAWINGS

FIG. 2A is a schematic perspective illustration of a camera of the imaging system, according to an embodiment of the present invention;

FIG. 2B and FIG. 2C are schematic sectional views of the camera, according to an embodiment of the present invention;

DETAILED DESCRIPTION OF EMBODIMENTS

Overview

Figure 1:
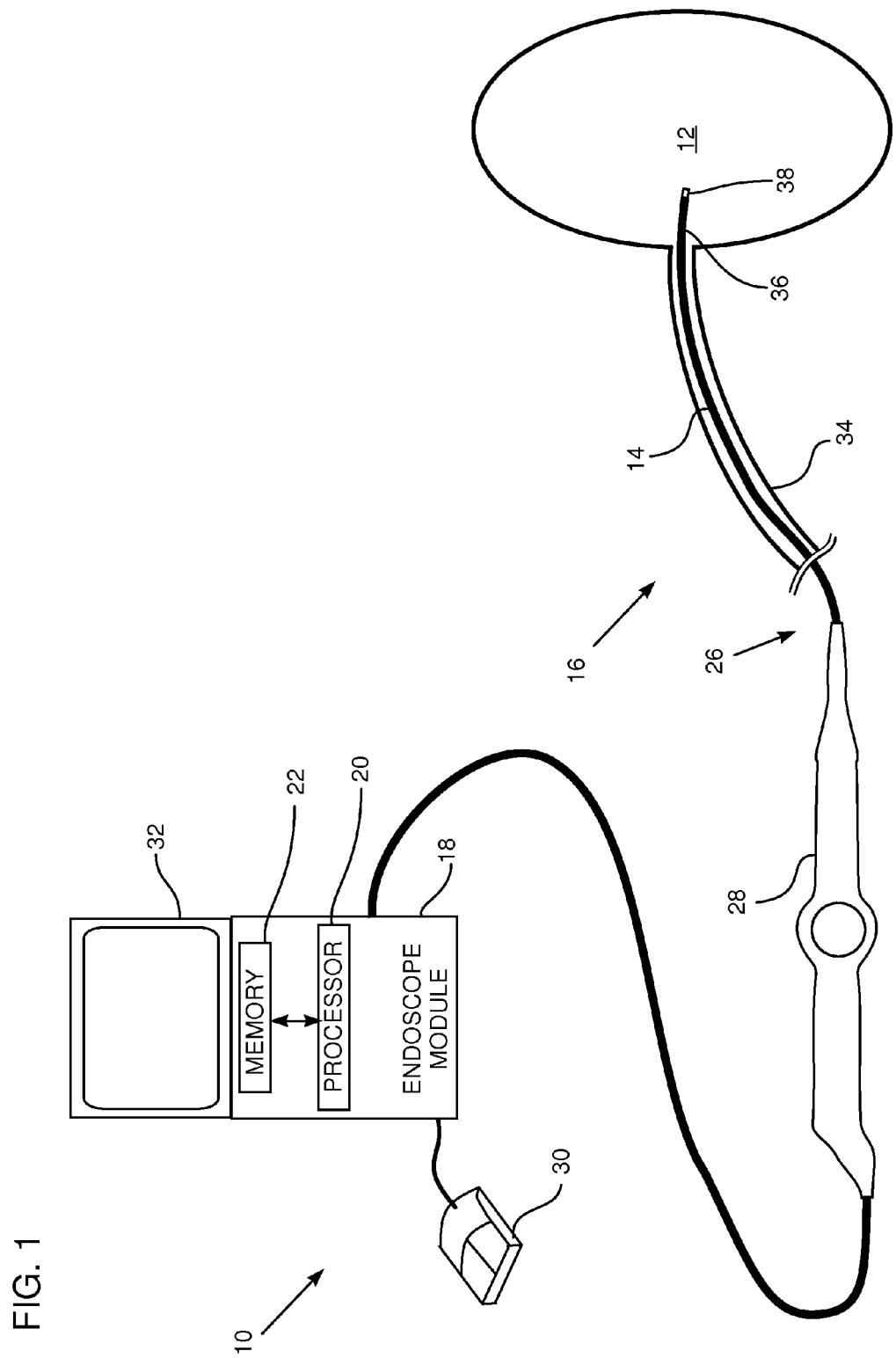
FIG. 1 is a schematic illustration of an endoscopic imaging system, according to an embodiment of the present invention.

Endoscopes used in surgery preferably have small dimensions. Especially for minimally invasive surgery, the smaller the dimensions, such as the diameter of the endoscope, the less the trauma on patients undergoing the surgery. A system which enables a reduction in diameter of the endoscope, without a concomitant reduction in efficiency of operation of the endoscope, would be advantageous.

An embodiment of the present invention provides an endoscope camera of extremely small dimensions. The camera may be incorporated into a cylindrical enclosure which is typically part of a tube configured to traverse a lumen of a patient during surgery. In embodiments of the present invention, the enclosure diameter may be of the order of 1 mm.

The camera comprises an imaging array which is mounted within the enclosure so that a plane face of the array is parallel to an enclosure diameter. Typically, the array is also mounted so that the plane face is parallel to an axis of the enclosure.

The camera also comprises a right-angle transparent prism having a rectangular entrance face, an exit face, and an hypotenuse configured to reflect radiation from the entrance face to the exit face. Typically the prism is isosceles having congruent entrance and exit faces. A first edge of the entrance face is longer than a second edge. The prism is mounted within the enclosure so that the first edge is parallel to the enclosure diameter and so that the exit face of the prism mates with the plane face of the imaging array; typically the prism is mounted to the array using optical cement.

The camera further comprises optics, which are typically mounted to mate with the entrance face of the prism. The optics receive incoming radiation from an object to be imaged by the camera, and the incoming radiation transmits through the prism entrance face, reflects from the hypotenuse of the prism, then transmits through the exit face to the imaging array.

The optics are typically anamorphic optics, having different magnifications in orthogonal directions. The different magnifications are selected so that the image of an object having a predetermined aspect ratio, such as a "standard" aspect ratio of 4:3, completely fills the exit face of the prism. (Except for the case where an aspect ratio of the exit face is the same as the aspect ratio of the object, the complete filling of the exit face requires the different magnifications.)

The anamorphic optics consequently optically distort the image formed on the array. The camera typically comprises circuitry, coupled to the array, which receives the image from the array in the form of a distorted frame, or set, of pixel values. The circuitry may be configured to apply an "un-distortion" numerical factor to the distorted frame, so as to generate an undistorted frame of pixels. The undistorted frame of pixels may be used to display an undistorted image of the object, i.e., the displayed image has the same aspect ratio as the object aspect ratio.

The combination of a right-angle prism having faces with the unequal edges, mounted onto an imaging array, enables implementation of endoscope cameras with millimeter dimensions.

DETAILED DESCRIPTION

Reference is now made to FIG. 1, which is a schematic illustration of an endoscopic imaging system 10, according to an embodiment of the present invention. System 10 may be used in an invasive medical procedure, typically a minimally invasive procedure, on a body cavity 12 of a human patient in order to image part or all of the body cavity. By way of example, in the present description the body cavity is assumed to be the bladder of a patient, and body cavity 12 is also referred to herein as bladder 12. However, it will be understood that system 10 may be used to image substantially any human body cavity, such as the gastrointestinal organs, the bronchium, or the chest, or a non-human cavity.

System 10 comprises an imaging apparatus 14 which enables delivery of an endoscope 16 to bladder 12. Apparatus 14 is typically in the form of a tube which is able to traverse a lumen of a patient's body, so that apparatus 14 is also referred to herein as tube 14. Endoscope 16 is controlled by an endoscope module 18 having a processor 20 communicating with a memory 22. Apparatus 14 is connected at its proximal end 26 to a handle 28 which enables an operator, herein assumed to be a physician, of system 10 to insert the apparatus into the bladder as well as to manipulate the endoscope so as to acquire images of the bladder. In some embodiments of the present invention, rather than manual manipulation of endoscope 16 using handle 28, the endoscope is manipulated automatically, such as by scanning, so as to acquire its images.

The operator is able to provide input to module 18 via controls 30, which typically comprise at least one of a keyboard, a pointing device, or a touch screen. Alternatively or additionally, at least some of controls 30 may be incorporated into handle 28. For simplicity, controls 30 are herein assumed to comprise a mouse, so that the controls are also referred to herein as mouse 30.

The processor uses software, typically stored in memory 22, to control system 10. Results of the actions performed by processor 20 may be presented on a screen 32 to the operator of system 10, the screen typically displaying an image of bladder 12 that is generated by system 10. The image displayed on screen 32 is assumed to be rectangular, and to have a display aspect ratio (DAR) of s:1, where DAR is the ratio of the image width to the image height. Typically, although not necessarily, the DAR of the image corresponds to the physical dimensions of screen 32, and the image DAR may be one of the standard ratios known in the art, such as 4:3. A difference between the DAR of the image and the dimensions of the screen may be accommodated by incorporating black "bands" on the screen, as is done in projecting high definition images with an aspect ratio of 16:9 onto a screen with width:height dimensions 4:3. As is explained in more detail below, embodiments of the present invention are able to present undistorted images of an object viewed by system 10 on screen 32 for substantially any desired value of DAR.

By way of example, in the following description, except where otherwise indicated, DAR of screen 32 is assumed to be 4:3, and the image formed on screen 32 is assumed to be in a format of 768 pixels wide×576 pixels high.

The software for operating system 10 may be downloaded to processor 20 in electronic form, over a network, for example, or it may, alternatively or additionally, be provided and/or stored on non-transitory tangible media, such as magnetic, optical, or electronic memory.

To operate system 10, the physician inserts tube 14 through a urethra 34 until a distal end 36 of the tube enters the bladder. Distal end 36 of tube 14 comprises a camera 38. The structure and operation of camera 38 are described below with reference to FIGS. 2A-2E.

Figure 2C:
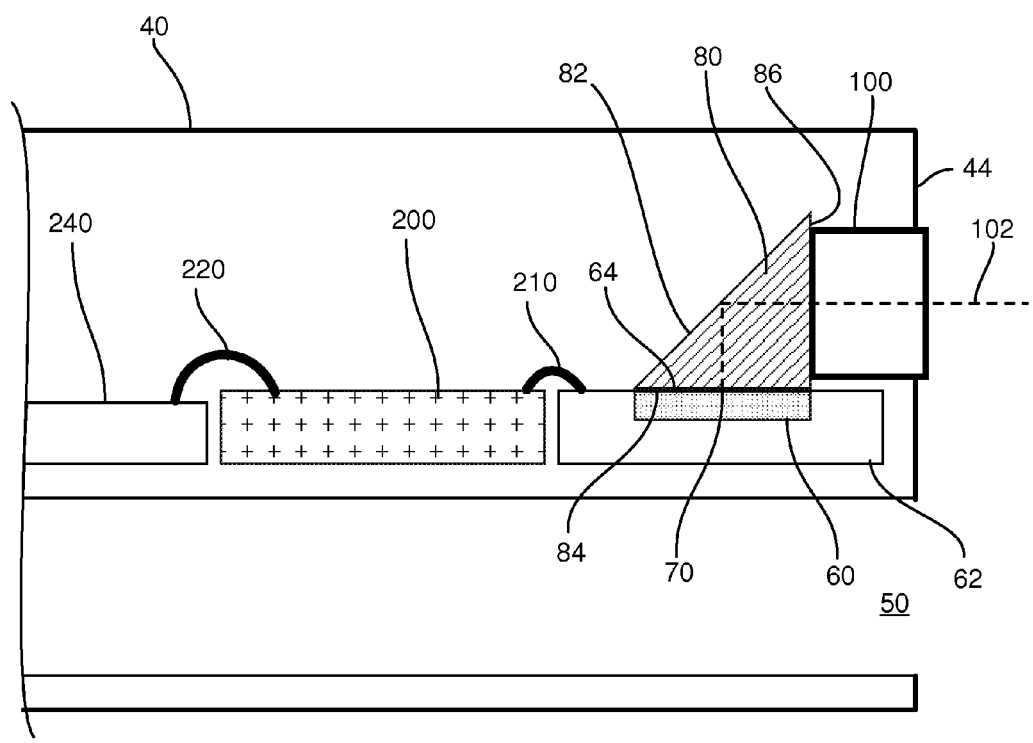
Figure 2D:
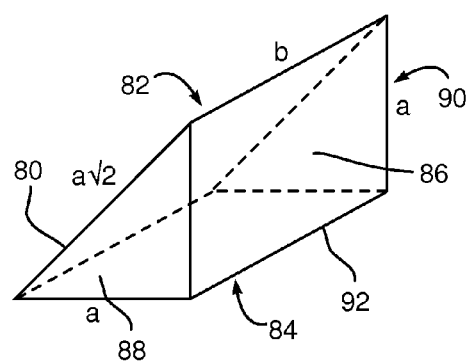
FIG. 2D is a schematic perspective view of an element of the camera, according to an embodiment of the present invention.
Figure 2E:
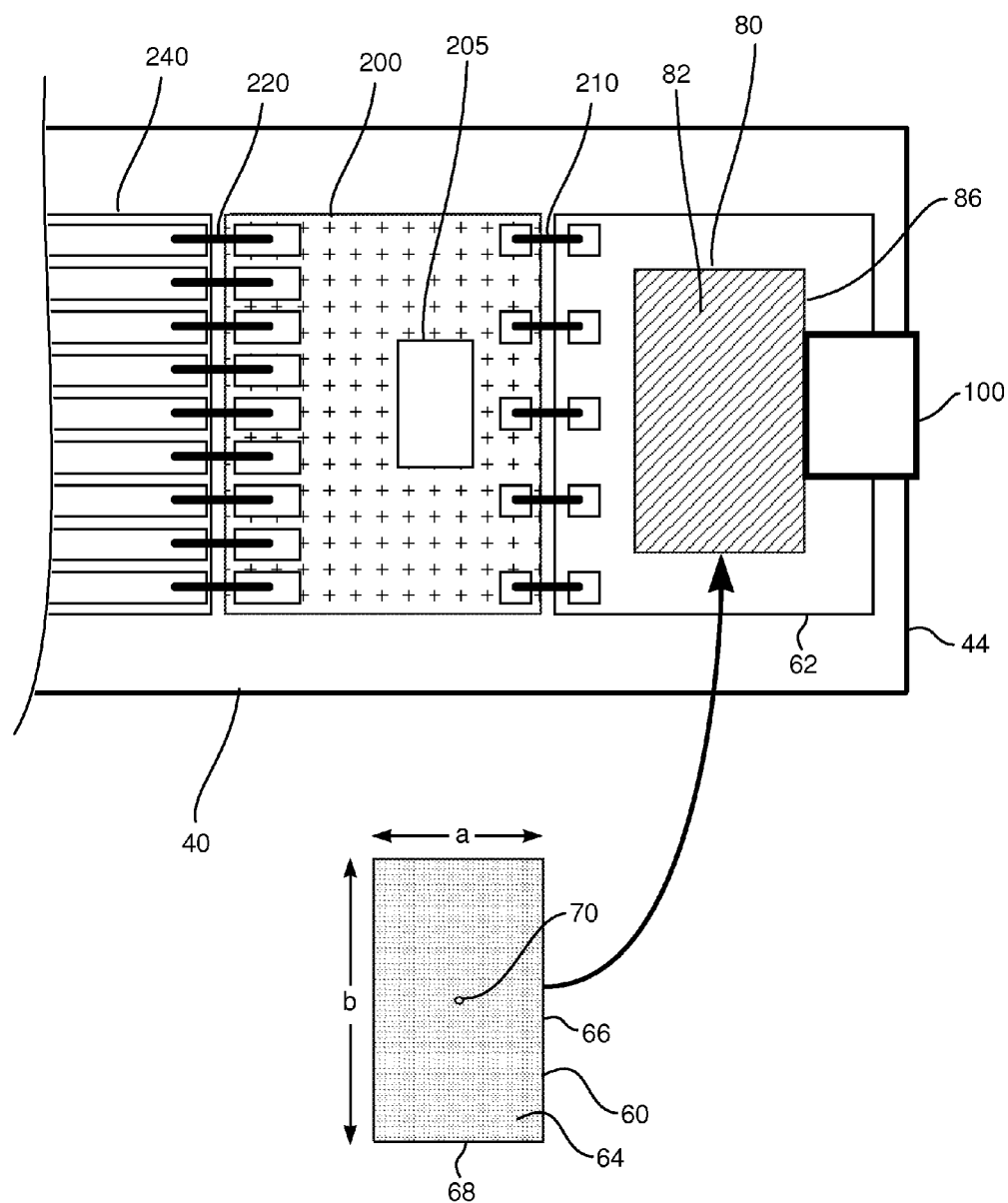
FIG. 2E is a schematic top view of elements of the camera, according to an embodiment of the present invention.

FIG. 2A is a schematic perspective view of camera 38, FIGS. 2B and 2C are schematic sectional views of the camera; FIG. 2D is a schematic perspective view of an element of the camera, and FIG. 2E is a schematic top view of elements of the camera, according to an embodiment of the present invention. Camera 38 comprises a cylindrical enclosure 40, having an internal enclosure diameter 42, the cylindrical enclosure being terminated at its distal end by an approximately plane surface 44. Typically, cylindrical enclosure 40 is integral with tube 14. For clarity in the description of camera 38, cylindrical enclosure 40 is assumed to define a set of xyz orthogonal axes, with the z axis corresponding to a symmetry axis 48 of the cylindrical enclosure, and the x axis in the plane of the paper in FIG. 2A. FIG. 2B is a schematic sectional view of camera 38 in an xy plane, the view being drawn with plane surface 44 removed.

Camera 38 comprises four generally similar light channels 46, which traverse tube 14 and which, at the distal end of the tube, are approximately parallel to the z axis. Channels 46 exit surface 44, and the channels are typically tubes which contain fiber optics (not shown in the diagram) for transmitting light that exits from surface 44. The light from the fiber optics illuminates elements of cavity 12, and returning light from the illuminated elements is used by camera 38 to generate an image of the elements, as described below. Alternatively, in some embodiments light channels 46 are fiber optics.

Camera 38 also comprises a working channel 50 which traverses tube 14, and which, at the distal end of the tube, is approximately parallel to the z axis. Working channel 50 is typically larger than light channels 46, and may be used by the physician to insert a variety of surgical tools, such as a biopsy tool, into cavity 12.

Camera 38 generates its images in a rectangular array 60 of imaging pixels, the array being mounted within enclosure 40. The rectangular array is typically a charge coupled device (CCD) that is formed on a planar substrate 62, the planar substrate acting as a supporting frame for the array. Array 60 has a face 64 which receives radiation forming the images generated by the array. The array has two edges, a first edge 66 having a length "b," and a second edge 68 having a length "a."

In embodiments of the present invention the two edges of array 60 are unequal in length, i.e., a ≠ b, and for clarity in the disclosure, edge 66 is assumed to be longer than edge 68, i.e., b>a, so that edge 66 may also be referred to as the longer edge or the width, and edge 68 may also be referred to as the shorter edge or the height. Array 60 has an array aspect ratio (AAR) of b:a, and if the pixels of array 60 are square, then a pixel aspect ratio (PAR) of array 60, corresponding to the ratio of the number of pixels in a row to the number of pixels in a column, is also b:a. Rectangular array 60 has a center of symmetry 70.

In a disclosed embodiment array 60 has b=500 μm and a=280 μm, and the array is formed of 2.5 μm square pixels. In this case the pixel dimensions of the array are 200×112, and AAR=PAR=500:280=200:112. Arrays with dimensions similar to these are known in the art, and may be supplied by imaging sensor providers, such as Forza Silicon Corporation, of Pasadena, CA.

Planar substrate 62 is mounted within enclosure 40 so that axis 48 of the enclosure is parallel to face 64 of the rectangular array, and so that the longer edge of the array is parallel to diameter 42.

As shown in FIGS. 2C and 2D, a right-angle transparent prism 80 is mounted within enclosure 40. Prism 80 has three rectangular faces: a hypotenuse face 82, a base face 84, also herein termed exit face 84, and an upright face 86, also herein termed entrance face 86. The prism also has a first isosceles right-angle triangle face 88 and a second isosceles right-angle triangle face 90. The dimensions of prism 80 are implemented so that exit face 84 has the same dimensions as array 60, i.e., the exit face is a rectangle having edge lengths a and b. Entrance face 86 has the same dimensions as exit face 84, i.e., the entrance face is a rectangle having edge lengths a and b. Entrance face 86 and exit face 84 have a common edge 92 with length a, i.e., the common edge is a longer edge of the exit and entrance faces.

The lengths of the sides forming the right angle of isosceles right-angle triangle face 88, and of isosceles right-angle triangle face 90, correspond to the length of the shorter edge of array 60, so that the two isosceles triangles of faces 88, 90, have lengths: a, a, a√2. Rectangular hypotenuse face 82 has edge lengths a√2, b.

Prism 80 is mounted onto array 60 so that exit face 84 mates with the array, i.e., so that the shorter edge of the exit face aligns with the shorter edge of the array, and so that the longer edge of the exit face aligns with the longer edge of the array. The mounting of the prism onto the array may be implemented using an optical adhesive, typically an epoxy resin, that cements the prism to the array. Such a mounting reduces undesired reflections from the exit face of the prism, as well as from face 64 of the array.

Optical elements 100, herein termed optics 100, are mounted within enclosure 40 so that they align with the entrance face of prism 80. Typically, optics 100 are cylindrical as illustrated in the figures. Typically, the mounting comprises cementing optics 100 to entrance face 86 using an optical adhesive. Optics 100 have an optic axis 102, and the optics are mounted so that the optic axis, after reflection in hypotenuse 82, intersects center 70 of array 60.

Figure 3A:
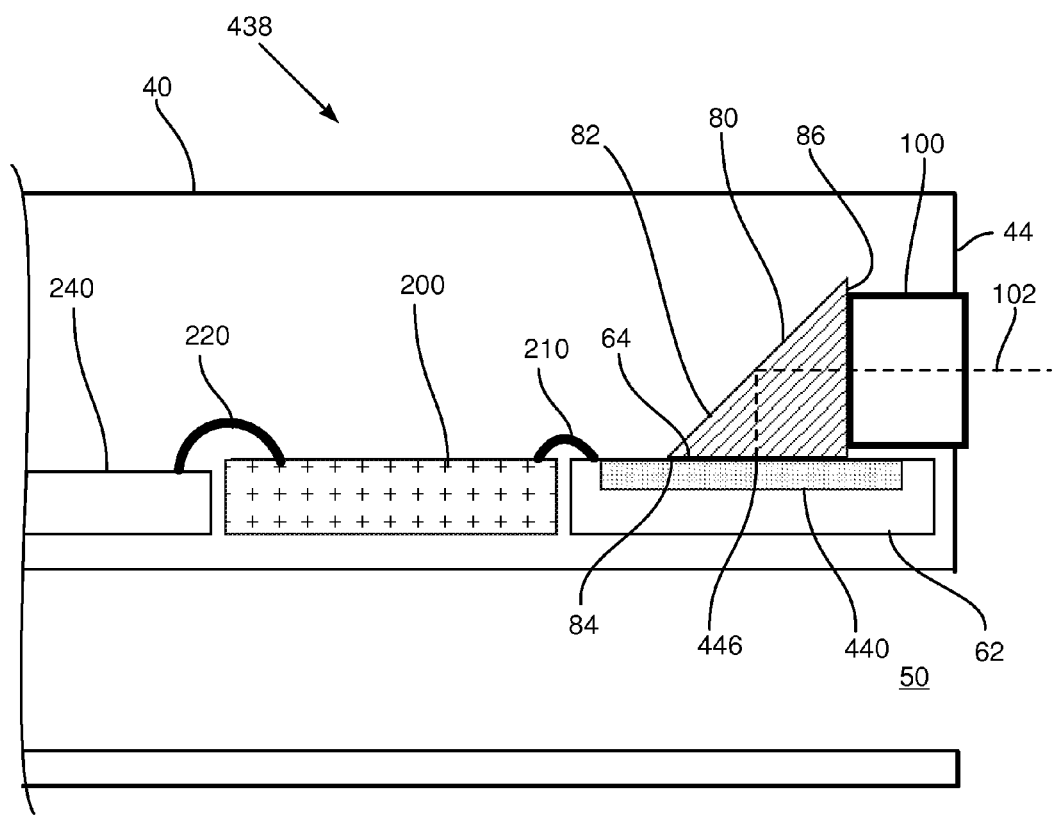
FIG. 3A is a schematic sectional view of an alternative camera.
Figure 3B:
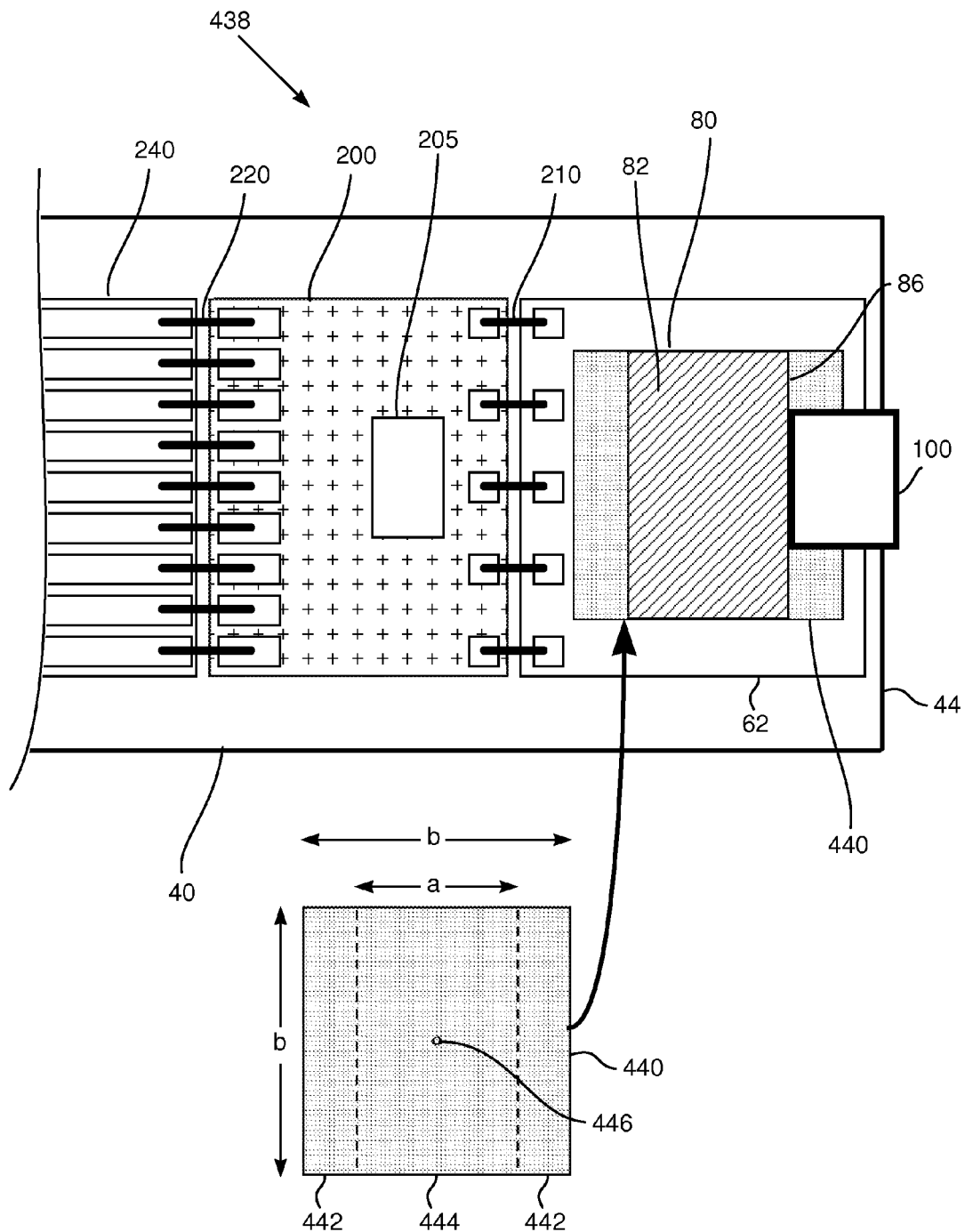
FIG. 3B is a schematic top view of elements of the alternative camera, according to an embodiment of the present invention.

FIG. 3A is a schematic sectional view of a camera 438, and FIG. 3B is a schematic top view of elements of the camera, according to an alternative embodiment of the present invention. Apart from the differences described below, the operation of camera 438 is generally similar to that of camera (FIGS. 2A-2E), and elements indicated by the same reference numerals in both cameras 38 and 438 are generally similar in construction and in operation.

In contrast to camera 38, which uses rectangular array 60 having unequal edges, camera 438 uses a square array 440. Square array 440 is configured to have its edge equal in length to the longer side of exit face 84, i.e., array 440 has an edge length b.

Prism 80 is mounted onto array 440 so that the shorter edges of the exit face align with the edges of the array. The mounting is typically symmetrical, so that as illustrated in FIG. 3B, there are approximately equal sections 442 which do not receive radiation from the exit face, and a rectangular section 444, having dimensions of b×a, which aligns with and is cemented to the exit face so as to receive radiation from the face. Optics 100 are mounted so that optic axis 102, after reflection in hypotenuse 82, intersects a center of symmetry 446 of section 444.

In a disclosed embodiment array 440 has b=500 μm and the array is formed of 2.5 μm square pixels. In this case the pixel dimensions of the array are 200×200. (Arrays with dimensions similar to these are also known in the art, and may be supplied by imaging sensor providers, such as the provider referred to above.) In the disclosed embodiment section 444 has dimensions of 500 μm×280 μm and pixel dimensions of 200×112, corresponding to the parameters of camera 38.

When camera 438 operates, section 444 is an active region of array 440, acquiring images projected onto the section via the completely filled exit face of the prism, whereas sections 442 are inactive regions.

Figure 4:
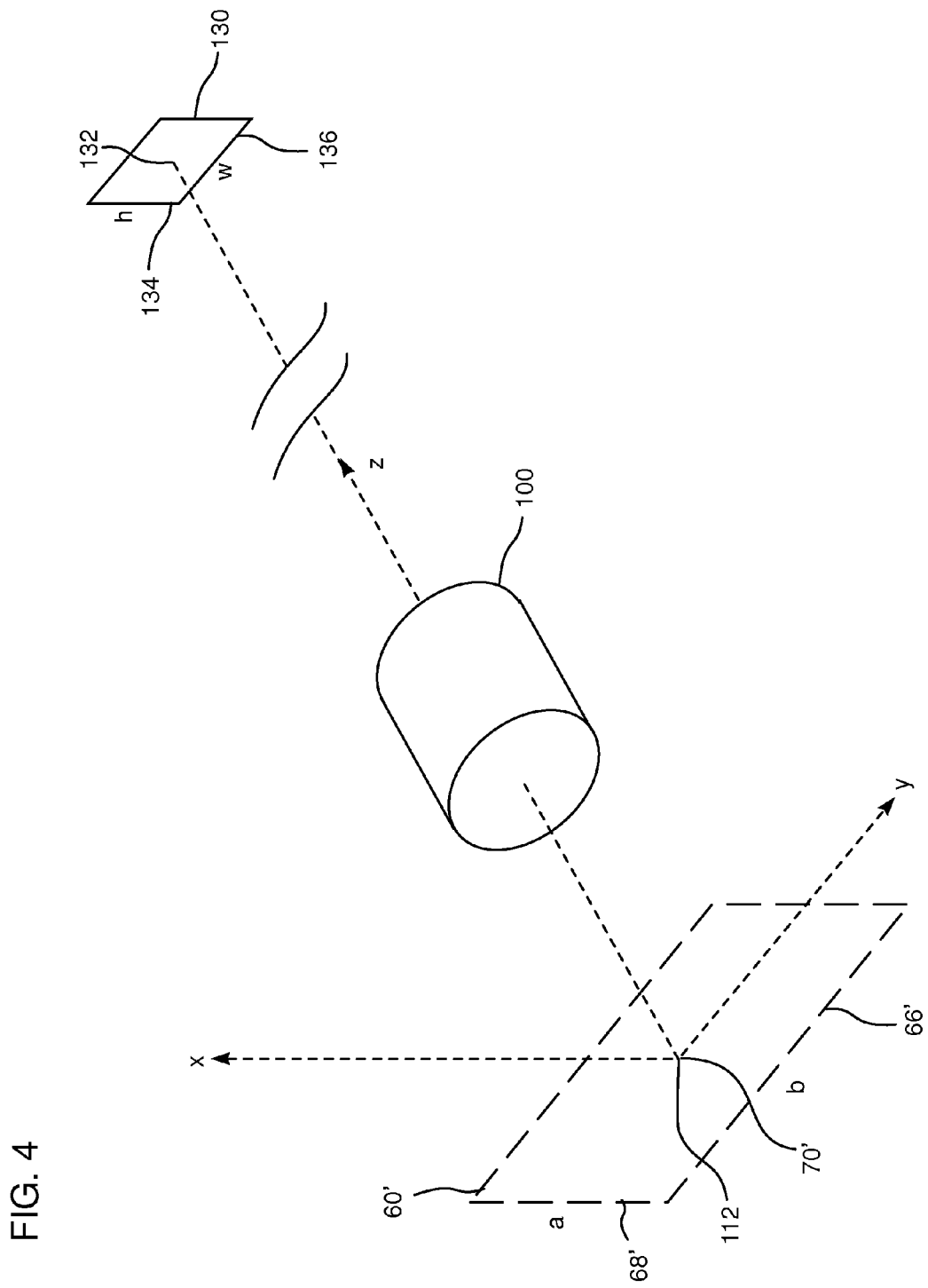
FIG. 4 is a schematic conceptual representation of the operation of optics of the camera of FIGS. 2A-2E, according to an embodiment of the present invention.

FIG. 4 is a schematic conceptual representation of the operation of optics 100, according to an embodiment of the present invention. The figure has been drawn using the set of xyz axes defined above for FIGS. 2A-2E, and assumes that camera 38 is being considered. Those having ordinary skill in the art will be able to adapt the following description for the case of camera 438. For simplicity, the figure has been drawn without the presence of prism 80, so that array 60 with center 70 is represented by a congruent array 60' with a center 70'. Array 60' has edges 66' and 68', corresponding to edges 66 and 68 of array 60. Edges 66' and 68' are parallel to the y and x axes, and center 70' is on the z axis. The following description reverts to referring to array 60 with center 70.

From a conceptual point of view, optics 100 may be considered to have the properties of an anamorphic lens, having different magnifications in the x direction and in the y direction. For simplicity the following description assumes that an object 130 is very distant from optics 100, so that the object is effectively at infinity, and those having ordinary skill in the art will be able to adapt the description for objects that are closer to optics 100. Furthermore, object 130 is assumed to be rectangular, with a center 132 on the z axis and edges 134 and 136 respectively parallel to the x and y axes. Edge 134 has a height h and edge 136 has a width w, giving an object aspect ratio of w:h.

Optics 100 is assumed to focus rays from center point 132 of object 130 to a focal point 112 on the z axis, and the optics are positioned so that center 70 of array 60 coincides with focal point 112. Object 130 may thus be completely in focus on array 60.

Typically, optics 100 are configured so that the image of object 130 completely fills the exit face of the prism and completely covers array 60; this configuration utilizes all the pixels of array 60. However, except for the case where w:h=b:a, the complete coverage entails optics 100 distorting the image of object 130, so that the image produced by the optics is no longer geometrically similar to the object. The distortion introduced by the optics is equivalent to the optics behaving as an anamorphic system, i.e., generating magnifications of the image on the array which are different in the x direction and in the y direction.

The magnifications for optics 100 are given by the following equations:

$$m_x = \frac{a}{h}; m_y = \frac{b}{w} \quad (1)$$

where $m_x$ is a height magnification of the optics, in the x direction, and $m_y$ is a width magnification of the optics, in the y direction.

A measure of the distortion produced by the optics is given by the ratio of the width:height magnifications in the two directions, i.e., a ratio of the width magnification $m_y$ to the height magnification $m_x$:

$$D = \frac{m_y}{m_x} = \frac{bh}{aw} \quad (2)$$

where D is a distortion metric for optics 100, equal to the ratio of the width:height magnifications.

As a first numerical example of the distortion introduced by optics 100, assume that object 130 has dimensions of w=4000 μm and h=3000 μm so that the object has an aspect ratio of 4:3. This aspect ratio is a typical value for "standard" imaging optics. Assume further that array 60 has the dimensions of the disclosed embodiment above, i.e., a width of 500 μm and a height of 280 μm. In this case, from equation (1), optics 100 are configured to have the following magnifications:

$$m_x = \frac{280}{3000} = 0.093; m_y = \frac{500}{4000} = 0.125 \quad (3)$$

From equation (2), the ratio of the width:height magnifications, the distortion D, of optics 100 in this case is:

$$D = \frac{bh}{aw} = \frac{500 \cdot 3000}{280 \cdot 4000} = 1.34 \quad (4)$$

As a second numerical example, assume that object 130 is square, so that w=h, corresponding to an aspect ratio of 1:1. In this case the distortion D introduced by optics 100, from equation (2), is equal to the aspect ratio of array 60, i.e., for the disclosed embodiment above, $$D = \frac{b}{a} = \frac{500}{280} = 1.79 \quad (5)$$

As a third numerical example, assume that object 130 has an aspect ratio of b:a, equal to the aspect ratio of array 60. In this case there is no distortion introduced by optics 100, i.e., the magnifications in the x and y directions are equal, $m_x = m_y$, and D=1.

The description of optics 100 above has referred to the height and width magnifications, $m_x$, $m_y$ in the x and y directions, required by the optics in order to image object 130 onto array 60. For each specific magnification, there is a corresponding focal length $f_x$, $f_y$ of optics 100. An approximation for the focal lengths may be determined from equation (6) for a simple lens:

$$f = \frac{md_o}{m+1} \quad (6)$$

where f is a required focal length of optics 100,
$d_o$ is the distance from the optics to object 130, and
m is a desired magnification.

Those having ordinary skill in the art will be able to use equation (6), or other equations well known in the optical arts, in order to calculate focal length $f_x$, $f_y$ of optics 100, and to calculate other parameters for the optics and for system 10.

Optics 100 may be implemented using individual "conventional" components or lenses, or even as a single lens, by methods which are well-known in the art. For example, U.S. Pat. No. 4,684,222, referenced above, describes a method for producing small anamorphic lenses. Alternatively or additionally, optics 100 may be implemented using gradient-index (GRIN) optics, using methods known in the art. Using GRIN optics allows a face of optics 100 that is to mate with prism entrance face 86 to be made plane, facilitating the cementing of the optics to the entrance face. In addition, GRIN optics may reduce the size of optics 100 compared to the size required by conventional components.

Returning to FIGS. 2C and 2E, circuitry 200, which is typically implemented as an integrated circuit, generates clocking signals which drive array 60 and which are provided to the array by connectors 210. Circuitry 200 is driven by a local processor 205, which has overall control of the operation of the circuitry. Signals generated by the array in response to radiation incident on the array are transferred by connectors 210 to circuitry 200. The signals generated by array 60 are initially in analog form, and circuitry 200, inter alia, amplifies and digitizes the analog signals, typically to form frames of digital images, corresponding to the optical images incident on array 60. Circuitry 200 then transfers the digitized frames to processor 20 (FIG. 1) via conducting elements 220. At least some of elements 220 are typically formed on, or are connected to, a flexible printed circuit board 240 which is installed in tube 14. However, any other method known in the art, such as using fibre optics and/or a wireless transmitter, may be implemented to transfer data generated by circuitry 200 to processor 20.

The digitized images output from array 60 have been optically distorted by optics 100 according to the distortion metric D, defined above with respect to equation (2). In order to display the images acquired by array 60 in an undistorted manner on screen 32, circuitry 200 applies a numerical "un-distortion" factor U to the received digitized images, so that the digitized images received by processor 20 are in an undistorted format. Alternatively, the un-distortion factor U may be applied by processor 20 to the distorted digitized images output by circuitry 200.

An expression for the un-distortion factor U is given by equation (7):

$$U = \frac{1}{D} = \frac{m_x}{m_y} \quad (7)$$

In other words, from equation (7), the ratio of the width:height magnifications, U, applied to the digitized images output from array 60, for display on screen 32, is the inverse of the ratio of the width:height magnifications, D, generated by optics 100. An example for applying the required magnifications to the digitized images from array 60 is described below.

Figure 5:
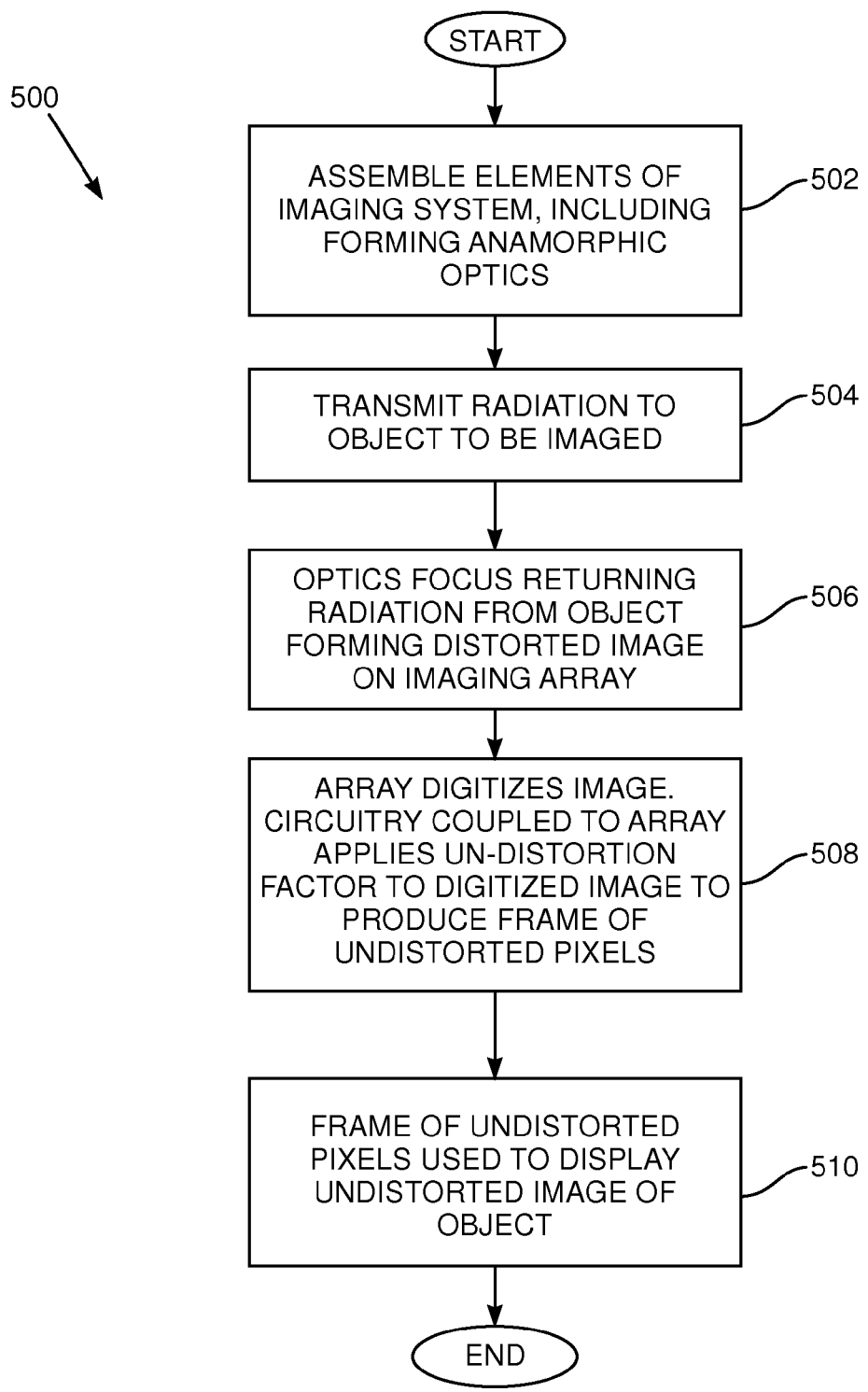
FIG. 5 is a flowchart describing steps in operation of the imaging system, according to an embodiment of the present invention.

FIG. 5 is a flowchart 500 describing steps in operation of system 10, according to an embodiment of the present invention. The steps of flowchart 500 assume that camera 38 is being used, and those having ordinary skill in the art will be able to adapt the description, mutatis mutandis, for the case of camera 438.

In an initial step 502, the elements of system 10 are implemented, generally as described above with respect to FIG. 1. The implementation includes forming optics 100, and the optics are typically formed according to equations (1)-(6) and the associated descriptions, for a predetermined object distance from the optics, a predetermined aspect ratio of the object, and a predetermined aspect ratio and size of array 60. Optics 100 are assumed to be anamorphic, having a distortion factor D, as defined by equation (2).

In an irradiation step 504 radiation is irradiated from optical channels 46 into cavity 12. Typically, although not necessarily, the radiation comprises light in the visible spectrum. However, in some embodiments the radiation comprises non-visible components, such as infra-red and/or ultra-violet radiation.

The radiation illuminates objects within cavity 12, including walls of the cavity, and returning radiation from the illuminated optics is acquired by optics 100.

In an image acquisition step 506 optics 100 receive incoming radiation from the illuminated objects. The optics focus the acquired incoming radiation to an image of the illuminated objects, the image being formed on array 60. The focusing of the radiation is performed by the optics transmitting the acquired incoming radiation to array 60 via entrance face 86 of prism 80, hypotenuse face 82 of the prism, and exit face 84 of the prism.

In a digital image step 508 array 60 and circuitry 200 digitize the image focused onto array 60, to form a frame, or set, of pixels of the distorted image. The circuitry then applies an un-distortion factor U, defined above by equation (7) to the frame of pixels, to generate a set of pixels representative of an undistorted image. The application of un-distortion factor U typically involves addition of pixels, removal of pixels, and/or change of value of pixels of the digitized image received from array 60, so as to produce a frame of digitized pixels in an undistorted format. The following examples explain how pixels of an undistorted image are generated.

A first example assumes that optics 100 image object 130, with an aspect ratio of 4:3, onto array 60, and that array 60 corresponds to the array of the disclosed embodiment referred to above, having an aspect ratio of 200:112. The image from array 60 is then "undistorted" by circuitry 200 to be suitable for display on screen 32 as a 768 pixels wide×576 pixels high image, i.e., as an image having the same aspect ratio as object 130.

Optics 100 are configured to have a distortion factor D corresponding to the first numerical example above, i.e. the ratio of the width:height magnifications is 1.34.

Circuitry 200 "undistorts" the digitized image from array by applying an un-distortion factor U, equal to $$\frac{1}{1.34} = 0.75$$

from equation (7). This factor corresponds to the ratio of width:height magnifications introduced by circuitry 200 into the pixels received from array 60

In the y direction, array 60 generates 200 pixels, and screen 32 displays 768 pixels in this direction, for a width magnification of 3.84.

In the x (height) direction, array 60 generates 112 pixels, and screen 32 displays 576 pixels in this direction, for a height magnification of 5.14. The ratio of the width:height actual magnifications, $$\frac{3.84}{5.14},$$

corresponds to the un-distortion factor U=0.75, introduced by circuitry 200.

A second example assumes that screen 32 has pixel dimensions of 1280×720, for an aspect ratio of 16:9. This aspect ratio substantially corresponds to the aspect ratio of array 60 (200:112). Thus an object with aspect ratio 16:9 may be imaged without distortion onto array 60, and there is no "undistortion" required in generating the 1280×720 pixels for screen 32. Since there is no distortion introduced by optics 100, the optics in this case may be spherical optics, or equivalent to spherical optics. In this second example the width magnification for screen 32 is $$\frac{1280}{200},$$

and the height magnification is $$\frac{720}{112},$$

both magnifications having the same value of approximately 6.4.

Consideration of the values above shows that for these examples circuitry 200 introduces pixels into the digitized values received from array 60, so as to produce a frame of pixels representative of an undistorted image. The introduction is typically by interpolation between the values from the array. Thus, in the y direction, circuitry 200 interpolates between the 200 values received to generate 768 pixels for the first example, or 1280 pixels for the second example, corresponding to the number of columns displayed by screen 32. Similarly, in the x direction, circuitry 200 interpolates between the 112 values received to generate 576 pixels for the first example, or 720 pixels for the second example, corresponding to the number of rows displayed by screen 32. The method of interpolation implemented by circuitry 200 may comprise any convenient interpolation method known in the art.

Those having ordinary skill in the art will be able to adapt the examples above to evaluate width and height magnifications introduced by circuitry 200 for other object aspect ratios, and for other array aspect ratios.

In a final display step 510, processor 20 receives from circuitry 200 a frame of pixels corresponding to an undistorted image of object 130, and displays the undistorted image on screen 32.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An endoscope camera, comprising:
a cylindrical enclosure having an enclosure diameter;
a rectangular array of imaging pixels formed on a planar substrate acting as a supporting frame for the array, which has a first side of a first length and a second side of a second length, wherein the first length is longer than the second length, and the array is mounted within the enclosure so that a plane face of the array is parallel to the enclosure diameter;
a right-angle transparent prism having a rectangular entrance face, an exit face, and an hypotenuse configured to reflect radiation from the entrance face to the exit face, the entrance face having a first edge of the first length and a second edge of the second length, the prism being mounted within the enclosure so that the first edge is parallel to the enclosure diameter with the exit face cemented to the plane face of the array; and
anamorphic optics, configured to receive incoming radiation from an object, mounted so as to transmit the incoming radiation to the array via the entrance and exit faces of the prism and to form an image on the array that is distorted responsively to an aspect ratio of the exit face.

2. The endoscope camera according to claim 1, wherein the optics comprise gradient-index (GRIN) optics.

3. The endoscope camera according to claim 1, wherein the optics have a circular cross-section.

4. The endoscope camera according to claim 1, wherein the optics focus the incoming radiation to have a first magnification and a second magnification orthogonal to and different from the first magnification.

5. The endoscope camera according to claim 4, wherein an optics-ratio of the first magnification to the second magnification is responsive to a prism-ratio of the first edge to the second edge.

6. The endoscope camera according to claim 4, wherein a ratio of the first magnification to the second magnification is responsive to an aspect ratio of an object imaged by the camera.

7. The endoscope camera according to claim 1, and comprising a processor which applies an un-distortion factor to the distorted image so as to produce an undistorted image of the object.

8. The endoscope camera according to claim 7, wherein the processor is configured to apply the un-distortion factor as a numerical factor.

9. The endoscope camera according to claim 1, wherein the right-angle transparent prism comprises an isosceles prism.

10. The endoscope camera according to claim 1, wherein the array is mounted so that an axis of the cylindrical enclosure is parallel to the plane face of the array.

11. A method for forming an endoscope camera, comprising:
providing a cylindrical enclosure having an enclosure diameter;
mounting a rectangular array of imaging pixels formed on a planar substrate acting as a supporting frame for the array, which has a first side of a first length and a second side of a second length, wherein the first length is longer than the second length, and the array is mounted within the enclosure so that a plane face of the array is parallel to the enclosure diameter;
mounting a right-angle transparent prism within the enclosure, the prism having a rectangular entrance face, an exit face, and an hypotenuse configured to reflect radiation from the entrance face to the exit face, the entrance face having a first edge of the first length and a second edge of the second length, the prism being mounted within the enclosure so that the first edge is parallel to the enclosure diameter with the exit face cemented to the plane face of the imaging array;
configuring anamorphic optics to receive incoming radiation from an object and to form an image on the array that is distorted responsively to an aspect ratio of the exit face; and mounting the optics so as to transmit the incoming radiation to the array via the entrance and exit faces of the prism.

12. The method according to claim 11, wherein the optics comprise gradient-index (GRIN) optics.

13. The method according to claim 11, wherein the optics have a circular cross-section.

14. The method according to claim 11, and comprising the optics focusing the incoming radiation to have a first magnification and a second magnification orthogonal to and different from the first magnification.

15. The method according to claim 14, and comprising determining an optics-ratio of the first magnification to the second magnification in response to a prism-ratio of the first edge to the second edge.

16. The method according to claim 14, and comprising determining a ratio of the first magnification to the second magnification is response to an aspect ratio of an object imaged by the camera.

17. The method according to claim 14, and comprising applying an un-distortion factor to the distorted image so as to produce an undistorted image of the object.

18. The method according to claim 17, wherein the un-distortion factor is a numerical factor.

19. The method according to claim 11, wherein the right-angle transparent prism comprises an isosceles prism.

20. The method according to claim 11, and comprising mounting the array so that an axis of the cylindrical enclosure is parallel to the plane face of the array.

* * * * *